United States Patent [19]
Dufresne et al.

[11] Patent Number: 4,662,975
[45] Date of Patent: May 5, 1987

[54] APPARATUS FOR DETERMINING THE ETCH RATE OF NONCONDUCTIVE MATERIALS

[75] Inventors: Ralph E. Dufresne, Auburn; Douglas A. Brauns, Federal Way, both of Wash.

[73] Assignee: The Boeing Company, Seattle, Wash.

[21] Appl. No.: 827,711

[22] Filed: Feb. 10, 1986

[51] Int. Cl.$^4$ .................... B44C 1/22; C03C 15/00; B29C 37/00

[52] U.S. Cl. .................... 156/345; 156/627; 156/644; 156/902; 324/437; 324/446

[58] Field of Search .............. 422/68; 324/443, 437, 324/446, 449; 156/345, 626, 627, 644, 902; 204/129.2

[56] References Cited

U.S. PATENT DOCUMENTS

| | | | |
|---|---|---|---|
| 2,291,022 | 7/1942 | Burbridge | 200/52 |
| 2,414,912 | 1/1947 | Wiatt | 200/52 |
| 2,701,183 | 2/1955 | Powers, Jr. et al. | 422/68 |
| 2,762,036 | 9/1956 | Triman | 340/267 |
| 2,821,603 | 1/1958 | Shepherd, Jr. | 200/133 |
| 2,933,675 | 4/1960 | Hoelzle | 324/443 |
| 3,023,153 | 2/1962 | Kurshan | 204/143 |
| 3,356,801 | 12/1967 | Caretto | 201/61.08 |
| 3,553,052 | 1/1971 | Jubb, Jr. | 156/345 |
| 3,909,331 | 9/1975 | Cohen | 156/253 |
| 3,959,046 | 5/1976 | Bussmann et al. | 156/345 X |
| 4,178,855 | 12/1979 | McVay et al. | 102/262 |
| 4,510,674 | 4/1985 | Izu et al. | 156/627 X |

FOREIGN PATENT DOCUMENTS

| | | | |
|---|---|---|---|
| 4003550 | 1/1984 | Japan | 156/627 |
| WO81/646 | 3/1981 | PCT Int'l Appl. | 156/627 |

Primary Examiner—William A. Powell
Attorney, Agent, or Firm—Christensen, O'Connor, Johnson & Kindness

[57] ABSTRACT

A probe that is used to determine the etch rate of a nonconductive material is comprised of a substrate of the material itself, plated on opposite sides with a conductive material. A first side of the probe has a small area of the plating removed to expose the substrate. The other side has an annular portion of the plating removed to define a wafer of plating isolated from the remainder of the plating. A lead wire is connected to the wafer and the entire second side of the probe is coated with an insulating mask. The probe is immersed in a bath of the etching solution. A voltage source is connected to the probe and to an electrode also immersed in the bath. A measurement device is connected in the circuit to detect current flow. When the etching bath dissolves the substrate through the exposed portion, a circuit is completed with the lead wire and the current flow is detected. The time from immersion of the probe to the beginning of current flow is used to calculate etch rate. Preferably the probe in constructed so that it remains in the bath in a passive state until actuated from a remote control circuit. In this manner, a plurality of probes can be placed in the bath and activated seriatim to conduct periodic etch rate measurements.

20 Claims, 7 Drawing Figures

APPARATUS FOR DETERMINING THE ETCH RATE OF NONCONDUCTIVE MATERIALS

BACKGROUND OF THE INVENTION

This invention relates to apparatus for determining the physical characteristics of materials and, in particular, to an apparatus for determining the rate at which a particular solution will etch a nonconductive material. The invention is particularly useful in the production of printed circuit boards.

Printed circuit board manufacture requires chemical cleaning of epoxy smear from drilled holes in the printed circuit board prior to copper plating. Typically, the smear of epoxy that finds it way into the drilled holes is removed by immersing the printed circuit board in a chemical solution that dissolves or etches the epoxy material. It is necessary to precisely monitor and control the etch rate of the epoxy so that there is consistent quality of the final product. One method presently used to monitor the etch rate is to perform a manual gravimetric analysis that is accomplished by weighing a small piece of the epoxy material, known in the art as a coupon, before and after a timed immersion in the etching solution. While this method does provide data from which the etech rate of the epoxy in the solutoin can be determined, it requires several steps and calculations, which makes the method slow, labor-intensive and not easily adaptable to on-line automated operation.

It is advantageous to provide a system in which the etch rate of the material in the solution can be tracked over a period of time by automatic actuation of several test probes periodically over a length of time. It is therefore an object of the present invention to provide a method and apparatus in the form of a test probe adaptable to determine the etch rate of nonconductive materials in an etching solution. The probe is configured to provide sufficient data to enable etch rate determination with a minimum of mathematical calculation and data recording. Also it is desirable to provide a measurement system that is easily automated for repeated measurements occurring over a finite length of time.

SUMMARY OF THE INVENTION

In accordance with the above-stated objects, the present invention provides a probe useful in determining the dissolution or etching rate of a particular electrically nonconductive material by an etching solution, which is typically an electrolyte and therefore electrically conductives. The probe consists of a coupon of the electrically nonconductive material that is under test. In most cases, this will be epoxy of the type used to manufacture printed circuit boards but could be any nonconductive material. The coupon of material is laminated between first and second plates of an electrically conductive material. Again, in typical situations, this will consist of copper cladding of the type utilized in printed circuit boards but could, again, be any electrically conductive material that can be bonded to the nonconductive coupon. A first surface of the coupon has an area from which the electrically conductive material is removed. A second opposing surface of the coupon has an area of the electrically conductive material that is bordered by an open area to isolate it from the remainder of the electrically conductive plating on the second surface of the coupon. Typically, the open area on the first surface of the coupon and the isolated area on the second surface of the coupon will be in alignment with one another. A lead wire is electrically and mechanically connected to the isolated conductive area on the second surface of the coupon, such as by soldering. The entire second surface of the coupon is covered by a mask of insulating sealant so that the electrically conductive plating, the isolated portion of the plating, and the electrical connection of the lead wire to the isolated portion are all enclosed in a layer of the sealant material.

The probe, as constructed above, is used in a system that includes a bath of the etching solution in which the probe in immersed. The lead wire from the probe is insulated so that there is no electrical conductivity between the lead wire and the etching solution. The lead wire is then connected to one terminal of a power source, such as a battery. The other terminal of the battery is connected to one end of a fixed resistance, the other end of the resistance being connected to an electrically conductive electrode, such as a platinum electrode, which is also immersedc in the etching solution spaced from the test probe. Since the connection of the test lead to the isolated portion of the conductive material on the second surface of the test probe is covered by the insulating masking material, there is no electrical conductivity between the etching solution and the lead. There is, further, no electrically conductive path from the lead to the solution through the coupon, since the coupon is defined as being composed of an electrically nonconductive material. As the probe remains in the etching solution, however, the etching solution will act on the exposed area of the coupon that is in register with the opening in the plating of the first surface of the probe. After some time, which is dependent upon the thickness of the coupon and the etching rate of the solution acting on the material from which the coupon is made, a hole will be etched through the coupon of nonconductive material so that the etching solution will come into contact with the isolated area of conductive material at the second surface of the probe. When the solution contacts the conductive area, there will then be an electrical path from the platinum electrode through the etching solution to the lead wire attached to this isolated portion of the conductive surface so that current will flow through the circuit. A voltmeter or other voltage-sensitive device, such as a galvanometer, is connected across the resistance and when a current begins to flow through the circuit a reading will appear on the voltmeter to indicate that the etching solution has worked its way through the coupon of nonconductive material. Since the coupon is of known thickness, a determination of etching rate can be made by determining the amount of time it took from immersion of the probe in the etching solution to the time when a current started to flow through the circuit, as indicated by a reading on the voltmeter.

In some situations, it is desirable to periodically check the etching rate of an etching solution to determine what effect, if any, use of the solution in the etching process has had on its etching strength. For example, in the manufacture of circuit boards, as more and more of the boards are treated with the etching solution, the chemical makeup of the solution may change because of the dissolved materials that are constantly being added to the solution and, therefore, the etching rate of the solution will necessarily change with time as the composition of the solution changes. In such a situation, it is desirable to maintain a series of probes in the etching solution that can be activated as desired whenever it is necessary to determine the etch rate. To accomplish this, the present invention contemplates protecting the coupon from the etching solution until a measurement is desired. The protection is provided by a housing that surrounds the coupon. THe housing can be a small glass tube sealed at both ends. The glass tube containing the coupon is placed on the etching solution. A small explosive charge is present in the tip of the glass tube. Measurement is initiated by remotely triggering the explosive charge thereby shattering the tip of the tube which allows the etching solution to rise in the tube and contact the coupon. Alternatively, several probes could be placed on a mechanical means that can be indexed to immerse the probes seriatim into the solution over a period of time.

BRIEF DESCRIPTION OF THE DRAWINGS

The construction and operation of the present invention will be better understood by those of ordinary skill in the art and others upon reading the ensuing specification, when taken in conjunction with the appended drawings wherein.

DETAILED DESCRIPTION OF THE PREFERRED EMBODIMENT

Figure 1:
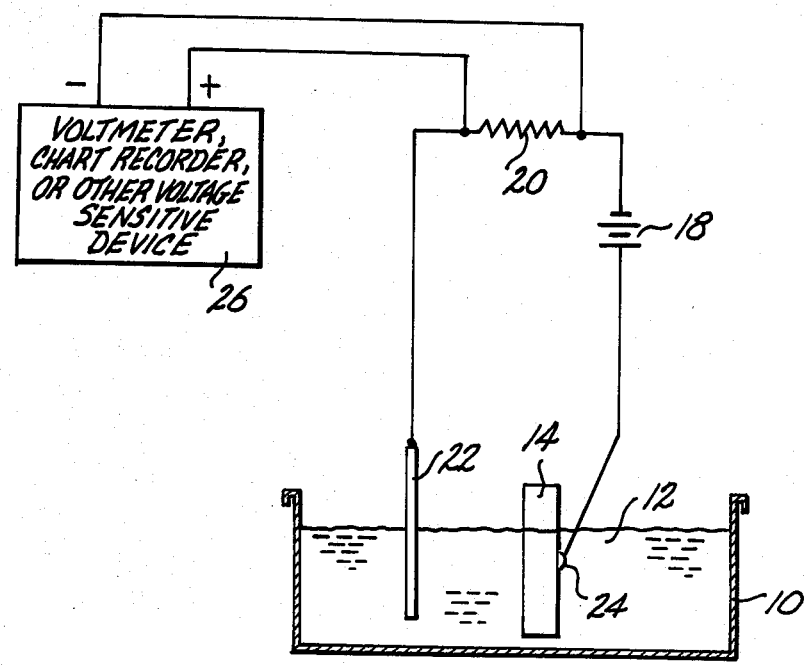
FIG. 1 is a schematic view of an etch rate measurement system made in accordance with the present invention.

FIG. 1 shows a schematic view of a testing system utilizing a probe made in accordance with the principles of the present invention in order to determine the etch rate of the nonconductive material that the probe is made of. The specifics of the test system and, more particularly, the specifics of the probe construction will be described in detail below; however, looking at FIG. 1, the system comprises a container 10 having a solution 12 contained therein. The solution 12 is an etching solution, typically an electrolyte, meaning that it is electrically conductive. A test probe 14, constructed in accordance with the principles of the present invention from material to be tested, is immersed in the solution 12. A lead wire 16 is connected from one surface of the test probe to the positive terminal of a voltage source, such as battery 18. The negative terminal of the battery 18 is connected to a fixed resistance 20 which, in turn, is connected to a cathode element, such as the platinum electrode 22 pictured in FIG. 1. The electrode 22 is also immersed in the solution 12. By definition, the probe 14 is constructed of a nonconductive material, therefore, there is no circuit path between the electrode 22 and the lead 16, which is connected to the test probe 14. As will be discussed below, the right-hand surface, as viewed in FIG. 1, of the test probe 14 and the connection of the lead 16 to the test probe 14 are insulated from the solution. As the solution etches away portions of the test probe 14, eventually the solution will produce a hole through the test probe so that the solution can come in contact with the electrical joint 24 at the interface between the lead wire 16 and the probe 14. At that time, an electrical current will flow between the electrode 22 and the lead 16, completing the circuit so that current flows through the circuit path shown in FIG. 1. A voltmeter 26 or other voltage-sensitive device is connected across the resistance 20 and measures the voltage drop across the resistance when current begins to flow through the circuit. By keeping track of the time when the probe 14 was first immersed in the test solution 12, and the time when current begins to flow through the circuit as indicated by the readings on the voltmeter 26, the time that it takes for the solution to etch through the probe 14 can be determined. SAince the probe 14 is of a known thickness, the etch rate of the material can be easily calculated.

Figure 2:
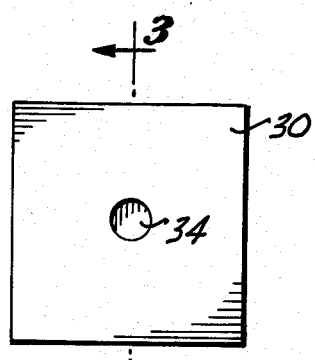
FIG. 2 is a front elevational view of a probe useful in the system shown in FIG. 1 and made in accordance with the principles of the present invention.
Figure 3:
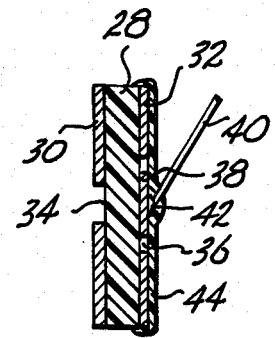
FIG. 3 is a sectional view along line 3—3 of FIG. 2 of one embodiment of the probe of the present invention.
Figure 4:
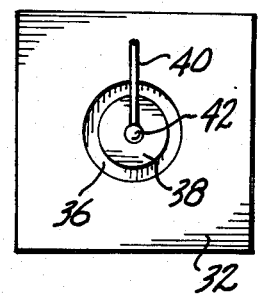
FIG. 4 is a rear elevational view of the probe of FIG. 2.

Turning now to FIGS. 2, 3, and 4, one embodiment of a test probe useful as the probe 14 in the test circuit of FIG. 1 is shown in orthographic projection. The test probe includes an epoxy substrate 28 having a copper cladding 30, covering a first surface of the substrate and a copper cladding 32, covering the second, opposing surface of the substrate. In the situation where the etching rate of a printed circuit board material is being measured, the test probe pictured in FIG. 3 is a small piece of "coupon" of the actual printed circuit board material. A portion of the copper cladding 30 is removed, exposing a portion 34 of the underlying substrate, as shown in FIGS. 2 and 3. The backside of the probe is shown in FIG. 4 and includes an annular void 36 where the copper cladding has been removed to isolate a central circular portion 38 of the copper cladding from the remaining cladding on the rear face of the coupon. A lead wire 40 is soldered as at joint 42 to the circular portion 38 of the cladding. A layer 44 of insulating masking material is laid down over the copper cladding 32 and covers the edges of the cladding as well as the joint area of the lead 40 where it is attached to the central portion 38. It can be seen in FIG. 3 that if the probe is utilized as the probe 14 in the circuit of FIG. 1, the insulating properties of the substrate 28 and the masking layer 44 will prevent any electrical circuit from forming between copper cladding 30 and copper cladding 32. However, when the etching solution eats its way through the epoxy substrate 28 where it is exposed to the solution by means of the opening in the copper cladding 30, the solution will come in contact with the circular portion 38. At that time, there will be electrical contact between the solution and the lead wire 40 that is soldered to the circular portion 38. Typically, the lead wire 40 is a Teflon-coated copper wire, the Teflon coating providing insulation from the solution.

Figure 5:
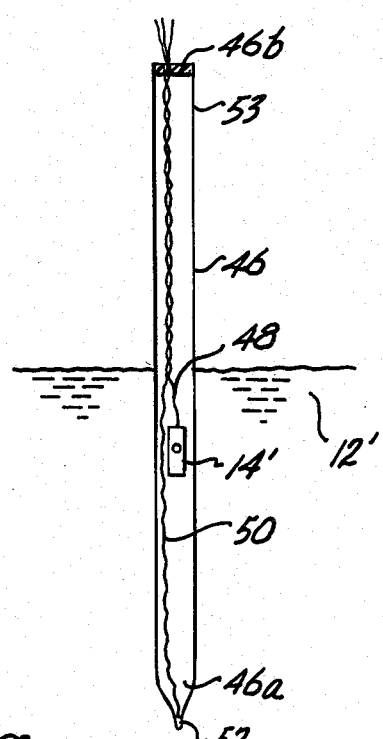
FIG. 5 is a side elevational view in section of the probe of FIG. 1 enclosed in a glass tube.

FIG. 5 illustrates another embodiment of a probe suitable for use as the probe 14 in the circuit of FIG. 1. The probe 14' in FIG. 5 is, in most respects, identical to the probe of FIGS. 2, 3 and 4. The probe 14' of FIG. 5, however, is enclosed within a glass tube 46 that is closed at the lower end. For example, the illustrated tube has a flame sealed tip 46a. The upper end of the tube has a group of lead wires that enter the tube in a sealed relationship to the upper wall 46b of the tube. The wires 48 are connected to the probe 14' while the wires 50 are connected to a small explosive charge 52 that is placed in the tip 46a of the tube. The wires 48 are connected to the measuring circuit of FIG. 1 while the wires 50 are connected to a detonating circuit, not shown, so that the charge 52 be remotely detonated.

In some situations, it is desirable that periodic checks be made of the etching rate of the etching solution in the circuit of FIG. 1 and it is therefore desirable to place several probes in the etching solution in a passive state and then be able to activate those probes in some predetermined sequence as measurements are needed. The probe of FIG. 5 allows this to be done. The probe 14' inside its glass tube 46 is partially immersed in the etching solution 12'. The probe 14' remains passive, as long as the glass tube 46 remains intact preventing any of the etching solution 12' from reaching the probe 14'. When it is desired to activate the probe, the explosive charge 52 is detonated, breaking the tip of the glass tube 46 and permitting the etching solution to reach the test probe 14'. The explosive charge can be any suitable material, for example, lead azide. A small pinhole 53 is formed in the tube wall above the solution level to bleed air out of the tube as the solution 12' enters through the shattered tip 46a.

Figure 6:
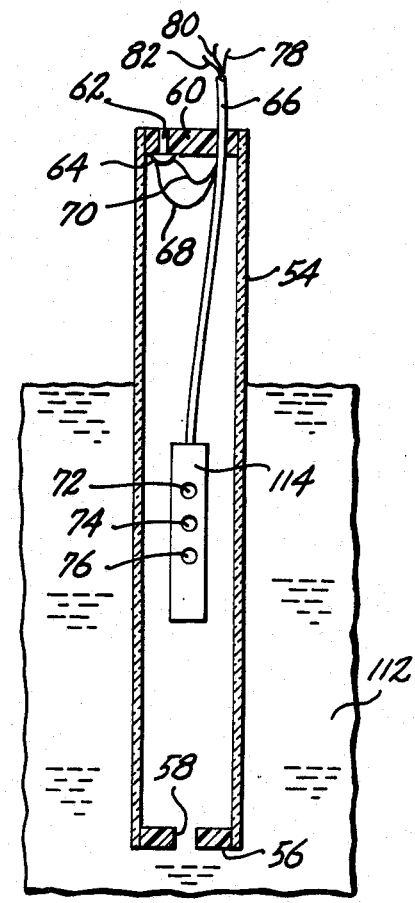
FIG. 6 is a front elevational view of another embodiment of a probe made in accordance with the principles of the present invention mounted within a glass cylinder.

Another embodiment of the probe is shown in FIG. 6 and is an embodiment that is also suitable for use in a situation where the probe remains passive for a predetermined time and then is activated by control circuitry. In FIG. 6, a probe 114 is shown surrounded by a glass cylinder 54. The bottom end of the cylinder 54 is closed by a plate 56, which has an opening 58 formed through it. The upper end of the cylinder 54 is closed by a second plate 60, which has an opening 62 formed through it; however, the opening 62 is blocked by a sealing means 64 mounted across the opening 62 on the interior of the glass cylinder 54. A control cable 66 leads from the probe 114 through the second plate 60 to the exterior of the glass cylinder 54. The cable is in sealed relationship within the second plate 60 so that the upper end of the cylinder 54 is effectively closed. The probe 114 and cylinder 54 are immersed in a solution 112 in a bath similar to that shown in FIG. 1. Because of the air trapped within the cylinder 54, and the sealed condition of the upper end of the cylinder, the solution will not enter the cylinder 54 so that the probe 114 is not in contact with the solution 112 as shown in FIG. 6. Lead wires 68 to 70, respectively, come from the cable 66 to the sealing means 64 that seals the opening 62 in the upper wall of the cylinder. In one embodiment of the invention, the sealing means 64 is an explosive charge that can be detonated by a signal passing through the leads 68 and 70 so that the sealing means is removed upon detonation, to unblock the opening 62. Likewise, the sealing means 64 could be some fusible material that melts upon receiving current through the leads 68 and 70 and, as it melts, unblocks the opening 62. In either case, once the opening 62 is unblocked, the air pressure within an without the cylinder 54 will equalize, such that the solution 112 will enter through the opening 58 in the plate 56 at the bottom of the cylinder and rise to the level of the solution outside the cylinder, covering the probe 114 and exposing it to the solution to begin the measurement of etch rate.

In actual practice, typically, the etch rate of the three separate probes is taken and then averaged to find the effective etch rate of the material being tested. FIG. 6 shows the probe 114 as having three open areas, 72, 74, and 76. The probe 114 is designed so that there are three separate etching areas exposed through these openings 72, 74, and 76, and individual lead wires 78, 80, and 82, coming through cable 66 are attached to the three areas to provide a multiple active-area probe.

Figure 7:
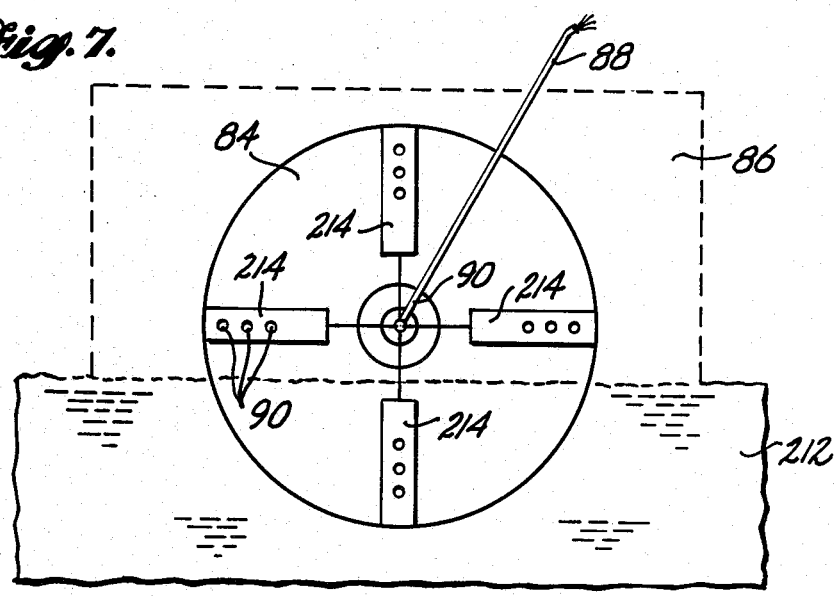
FIG. 7 is a front elevational view of an indexing means made in accordance with the principles of the present invention, having several probes mounted thereon for seriatim exposure to an etching solution.

FIG. 7 shows a further embodiment of the invention that allows sequential probes to be exposed to the etching solution for the carrying out of a sequence of etch rate measurement over a period of time. FIG. 7 shows a wheel 84 rotatably mounted on a suitable structure 86 so that a lower portion of the wheel 84 is immersed in an etching solution 212. Four probes 214 are radially arranged about the wheel so that as the wheel rotates different ones of the probes 214 are immersed in the etching solution 212. A cable 88 connects the control circuitry to some suitable commutator assembly 90, also mounted on the wheel that routes electric current to the desired probe 214 to allow etch rate measurement of only the probe that is immersed in the solution. The control circuitry is designed so that at desired intervals the wheel 84 is rotated to submerge one of the probes 214, allowing an etch rate measurement to be taken and then, at a later desired time, rotating the wheel again to expose the next probe in sequence to the etching solution for a further measurement of etch rate. In this manner, sequential etch rate readings can be taken at least four times, or more, depending on the precise configuration of the apparatus. The probes 214 can be of the type described in relation to FIG. 6, having three substrate exposure areas 92 on each probe to permit multiple measurements of etch rate with each probe for the purpose of obtaining an average etch rate for the material.

In summary, therefore, an apparatus for measuring the etch rate of a nonconductive material has been provided. In particular, a probe made of the material to be tested has been described and illustrated, along with a type of probe that can be passively maintained in the etching solution for any desired time and then remotely activated to allow etch rate measurements to be taken by several probes in a predetermined sequence. It will be understood by those of ordinary skill in the art and others that, while preferred embodiments of the probes of the present invention have been described and illustrated, several changes can be made in the illustrated and described embodiments without exceeding the scope of the present invention. For example, the particular material utilized in the illustrated embodiments was epoxy for the nonconductive material and copper cladding laminated on the substrate; however, other materials can be used in the probe, depending on the desires of the operator. Also, while the illustrated probes have been of rectangular or square configuration, other geometric shapes of probes are suitable, as well as other shapes for the test openings, which expose the epoxy substrate to the etching solution. Since many changes can be made in the illustrated embodiments, while remaining within the scope of the present invention, the invention should be defined solely with reference to the claims that follow.

The embodiments of the invention in which an exclusive property or privilege is claimed are defined as follows:

1. An etch rate measurement probe, comprising:
    a planar coupon of electrically nonconductive material, having first and second opposed surfaces;
    a first plate of electrically conductive material overlying and affixed to said first surface and having a first opening formed therein;

a second plate of electrically conductive material overlying and affixed to said second surface and having a second opening formed therein;

a wafer of electrically conductive material affixed to said second surface and lying within said second opening, said wafer being smaller than said second opening, and arranged within said opening such that it is spaced from the boundaries of said opening;

a lead wire electrically and mechanically connected to said wafer; and a coating of insulating masking material substantially completely covering said second plate, electrically conductive wafer, and the connection point of said lead to said electrically conductive wafer.

2. The probe of claim 1, wherein said coupon is comprised of epoxy.

3. The probe of claim 1, wherein said first and second plates and wafer are all comprised of the same material.

4. The probe of claim 3, wherein said first and second plates and said wafer are comprised of copper.

5. The probe of claim 1, wherein said lead wire is soldered to said wafer.

6. The probe of claim 1, wherein said first and second openings are substantially aligned with one another.

7. The probe of claim 6, wherein said first and second openings are circular and substantially coaxial.

8. The probe of claim 1, further including:
an enclosure of nonconductive material surrounding the probe; and
an explosive charge mounted within said enclosure.

9. The probe of claim 8, including a second lead wire electrically connected to said explosive charge.

10. The probe of claim 8, wherein said enclosure comprises a glass tube.

11. The probe of claim 8, wherein said explosive charge is comprised of lead azide.

12. The probe of claim 1, further including:
a cylinder of nonconductive material surrounding said probe having first and second ends;
a first wall closing the first end of said cylinder, said first wall having a first hole formed therethrough;
a second wall closing the second end of said cylinder, said lead wire passing through said second wall in sealed relation to it, said second wall having a second hole formed therethrough;
closure means covering said second hole, said closure means being remotely operable to uncover said second hole.

13. The probe of claim 12, wherein said closure means comprises an explosive charge.

14. The probe of claim 12, wherein said closure means comprises a fusible material.

15. A probe for measuring the etch rate of an electrically nonconductive material, including a substrate comprised of the material to be tested;
a plating of electrically conductive material on a first surface of said substrate, said plating having a plurality of openings formed therein to expose said substrate;
a plurality of leads paired with the openings in said first plating and affixed to a second surface of said substrate; and
a layer of insulating material covering a second surface of said substrate and the connection points of said leads to said substrate.

16. The probe of claim 15, wherein said substrate comprises epoxy.

17. The probe of claim 15, further including a plurality of conductive wafers affixed to said second surface of said substrate, isolated from one another, each of said leads being respectively connected to an associated one of said wafers.

18. The probe of claim 17, wherein said plating and said wafers are of the same material.

19. A system for measuring the etch rate of a nonconductive material comprising:
(a) a bath of electrolytic etching solution;
(b) an electrical voltage source;
(c) a resistance means connected at a first end thereof to one pole of said voltage source;
(d) an electrode connected to a second end of said resistance means and immersed in said bath;
(e) a voltage sensitive measurement device connected in parallel across said resistance means; and
(f) a probe connected to the other pole of said voltage source and immersed in said bath, said probe including a substrate of the nonconductive material to be tested, a first layer of conductive material overlying a first surface of said substrate, a portion of said layer removed to expose said substrate to said bath, a second layer of conductive material plated over a second, opposing surface of said substrate, a portion of said second layer removed to define and electrically isolate a second portion of said second layer, a lead wire connected to said second portion and to said voltage source, and, an insulating mask covering said second layer, second portion and the connection of said lead wire to said second portion.

20. The system of claim 19, further including a plurality of said probes mounted on an indexing means, said indexing means operable to selectively position desired ones of said probes in said bath in a predetermined sequence.

* * * * *

UNITED STATES PATENT AND TRADEMARK OFFICE
CERTIFICATE OF CORRECTION

PATENT NO. : 4,662,975

DATED : May 5, 1987

INVENTOR(S) : Ralph E. Dufresne et al.

It is certified that error appears in the above-identified patent and that said Letters Patent is hereby corrected as shown below:

Column 1, line 26: "etech" should be --etch--

"solutoin" should be --solution--

Column 1, line 50: "conductives" should be --conductive--

Column 2, line 19: "immersedc" should be --immersed--

Column 3, line 5: "THe" should be --The--

Column 4, line 20: "SAince" should be --Since--

Column 4, line 32: "of" should be --or--

Column 5, line 58: "an" should be --and--

Signed and Sealed this

Twentieth Day of September, 1988

Attest:

DONALD J. QUIGG

Attesting Officer

Commissioner of Patents and Trademarks